United States Patent
Dick et al.

(10) Patent No.: US 7,836,892 B2
(45) Date of Patent: Nov. 23, 2010

(54) METHOD FOR CONTROLLING A DEVICE FOR TREATING THE HUMAN EYE

(75) Inventors: Manfred Dick, Gefell (DE); Holger Maeusezahl, Jena (DE); Dan Reinstein, London (GB); Eckhard Schroeder, Eckental (DE); Hartmut Vogelsang, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 937 days.

(21) Appl. No.: 10/516,432

(22) PCT Filed: Jun. 2, 2003

(86) PCT No.: PCT/EP03/05755

§ 371 (c)(1),
(2), (4) Date: Jul. 29, 2005

(87) PCT Pub. No.: WO03/101355

PCT Pub. Date: Dec. 11, 2003

(65) Prior Publication Data

US 2006/0064078 A1    Mar. 23, 2006

(30) Foreign Application Priority Data

May 31, 2002   (DE) ............................... 102 24 493

(51) Int. Cl.
*A61B 19/00* (2006.01)
*A61B 18/20* (2006.01)

(52) U.S. Cl. ........................... 128/898; 606/4; 606/10; 351/212

(58) Field of Classification Search ................. 606/4–6, 606/10–12; 351/205–212; 128/898
See application file for complete search history.

(56) References Cited

U.S. PATENT DOCUMENTS

| 5,098,426 | A | | 3/1992 | Sklar et al. ..................... 606/5 |
| 5,777,719 | A | * | 7/1998 | Williams et al. ............ 351/212 |
| 5,782,822 | A | * | 7/1998 | Telfair et al. .................... 606/5 |
| 5,807,381 | A | | 9/1998 | Lieberman ..................... 606/5 |
| 5,843,070 | A | | 12/1998 | Cambier et al. ................ 606/5 |
| 6,129,722 | A | * | 10/2000 | Ruiz ............................. 606/5 |
| 6,296,634 | B1 | * | 10/2001 | McMillen et al. ............. 606/10 |
| 6,322,216 | B1 | * | 11/2001 | Yee et al. ..................... 351/210 |
| 6,394,999 | B1 | | 5/2002 | Williams et al. ................ 606/5 |
| 6,984,227 | B2 | * | 1/2006 | Munnerlyn et al. ............ 606/5 |
| 7,066,928 | B2 | | 6/2006 | Dick et al. |
| 7,111,938 | B2 | * | 9/2006 | Andino et al. ............. 351/212 |
| 7,130,835 | B2 | * | 10/2006 | Cox et al. ..................... 706/21 |

(Continued)

FOREIGN PATENT DOCUMENTS

DE    101 03 763    8/2002

(Continued)

*Primary Examiner*—Ahmed M Farah
(74) *Attorney, Agent, or Firm*—Leydig, Voit & Mayer, Ltd.

(57) ABSTRACT

A method for controlling a device for the treatment or refractive correction of the human eye using an electronic data processing system. The method provides a simple overview of the influence of all of the parameters. To this end, once the operating parameters have been determined, a graphical simulation of the operating procedure is carried out in the form of a graphical visualization.

11 Claims, 3 Drawing Sheets

U.S. PATENT DOCUMENTS

| | | |
|---|---|---|
| 2001/0020163 A1 | 9/2001 | Clapman ........................ 606/5 |
| 2004/0176753 A1 | 9/2004 | Dick et al. ..................... 606/4 |

FOREIGN PATENT DOCUMENTS

| | | |
|---|---|---|
| EP | 0 983 757 | 3/2000 |
| JP | 2000300596 | 10/2000 |
| JP | 2001269317 | 10/2001 |
| WO | WO 01/28476 | 4/2001 |
| WO | WO 02/07660 | 1/2002 |
| WO | WO 03/002047 | 1/2003 |

* cited by examiner

METHOD FOR CONTROLLING A DEVICE FOR TREATING THE HUMAN EYE

The present invention relates to a method for controlling a device for the ablation of parts of the human eye, in particular the cornea, by means of laser irradiation, the control being exercised by an electronic data-processing system which provides data to a device for treating the human eye by means of laser irradiation, and a device for treating the human eye by means of laser irradiation.

BACKGROUND

In ophthalmic surgery a series of methods are known which make possible, with or without additional invasive procedures, an abrasion of parts of the cornea surface to correct sight defects. In particular the PRK, LASIK and LASEK methods may be named here.

Traditionally, fine tuning of the refractive correction is carried out in the case of sphere and cylinder on the basis of subjective phoropter measurements, because the best possible standard correction can thereby take place in individually secured manner without taking higher aberrations into account. In the meantime, higher aberrations can be subjectively evaluated with the help of a so-called phase-plate phoropter which is known for example from DE10103763, or adaptive phoropters, and used for refractive correction.

A problem when carrying out such treatment procedures is the fact that slight changes in the treatment parameters can have a marked effect on the success of the treatment. Reliance is usually placed here on the experience of the doctor in attendance, the assumption being that he is aware of the significance of the effect of all the parameters.

SUMMARY OF THE INVENTION

An object of the present invention is therefore to provide a method for controlling a device for treating the human eye which provides a simple overview of the effect of all the parameters.

The present invention provides a method for controlling a device for an ablation of a part of a human eye using laser irradiation, the control being exercised using an electronic data processing system. The method includes the steps of determining optic and geometrical data of the eye, and performing a graphic simulation of the ablation in the form of a graphic visualization. It is provided according to the invention that once the optical and geometric eye data have been established a graphic simulation of the ablation is carried out in the form of a graphic visualization. During the graphic visualization, in particular the pachymetry of the cornea before and after the treatment procedure is represented graphically. The optical and geometric eye data are in particular thickness (pachymetry) and also the curvature of the cornea (topography). These data can be summarized for each eye in a pachymetry map and a topography map. In this way, the doctor in attendance can graphically anticipate the result of the treatment procedure and in particular recognize problem areas. In addition, problems that can be expected, such as too small a residual thickness of the cornea in part areas, can be established by the computer software used and displayed as a warning. In particular for the correction of several sight defects, an optimum parameter configuration can be discovered with the help of the method according to the invention, for example by varying one or more parameters. This makes it possible to optimize the ablation for example to a minimum abrasion of the cornea. All the parameters can be entered or automatically recorded by means of the computer software which contains all the reciprocal relationships and which can thus calculate a correction which takes all the relevant factors into account. However the weighting and selection of the parameters is not unequivocal, but determined by various patient-specific objectives; e.g. best sight during the day, best sight at dusk, smallest corneal abrasion or similar. The computer software preferably includes an operating interface with the help of which, using the weighting presented previously, the doctor can swiftly arrive at an optimum correction. A mode can also be selected which makes possible a manual adjustment of all parameters, e.g. via scroll boxes or similar displayed on the operating interface. The effect of the parameter changes is illustrated directly via a graphic simulation of the correction.

All the treatment parameters that are to be entered manually are preferably entered by means of a central input/output device. This can be for example a computer screen connected to a keyboard or a so-called touch screen.

In a development of the method according to the invention it is provided that the establishment of the operating parameters comprises one or more of the following process steps: establishment of topography data of the eye; establishment of refraction data of the eye; establishment of higher-order aberration data by wave-front measurement; establishment of pachymetry data; establishment of the pupillometry of the eye (preferably for various lighting conditions); point-accurate overlaying of all established measurement data in a fixed coordinates system of the eye; calculation of height data of the deviations relative to a reference surface; calculation of a height data difference relative to the reference surface; calculation of an adapted height data difference relative to the reference surface; calculation of ablation coordinates for the laser.

K values and/or a curvature map and/or a topography map and/or a power map are preferably obtained from the topography data. The spherical and/or cylindrical refraction correspondingly form part of the data for controlling the ablation device. The reference surface is freely selectable as regards the topography data, preferably an ellipsoid, in the case of the ellipsoid the reference surface of the refraction data is correspondingly a spheroid. When establishing the pupillometry, i.e. in particular the diameter of the pupil, parameters of the various lighting conditions are preferably included, as the pupil diameter changes depending on the lighting. The deviation of the centre of the pupil can thus shift by up to 0.5 mm under different lighting conditions. Additional parameters such as special patient wishes regarding visual acuity distribution or similar are included in the adapted height data difference. As a result of the overlaying of these measurement data in a fixed coordinates system of the eye, the overall correction of the eye can be shown in one representation.

In a development of the method according to the invention it is provided that in a further intermediate step, height data deviations of the cornea surface relative to a reference surface are calculated from the topography and/or refraction data. The height data are stored as a height data map of the deviations and can be visualized graphically.

In a development of the method according to the invention it is provided that in a further intermediate step the tissue to be abraded from the cornea is determined from the height data of the deviations of the cornea surface.

In a preferred version the device for treating the human eye includes a laser and/or means for wave-front measurement.

The present invention furthermore provides a device for treating the human eye by means of laser irradiation comprising an apparatus for measuring aberrometry, an apparatus for measuring topography, an apparatus for measuring pachymetry, optionally an apparatus for measuring pupillometry, an apparatus for point-accurate, centred overlaying of the measurement data of all the measuring equipment of a laser unit and also an electronic data-processing apparatus which by using a treatment model can link the measurement values and further patient data to ablation values. This device preferably also includes an apparatus for measuring the pupillometry of the eye, i.e. a pupillometer. The device preferably includes a measuring equipment arrangement which allows the measurement of aberrometry, topography, pupillometry and pachymetry by means of a fixing, i.e. in a point-accurate reference of the measurement data to a centred fixed coordinates system of the eye. For this, the device has a combination of the necessary measuring instruments which make possible a measurement of the eye to be treated via a common eyepiece or overlay all separate measurement data centred vis-à-vis a location-specific coordinates system and display them together in their interaction. This is preferably carried out by determining the optical axis or the visual axis of the eye during the measurements using each individual measuring apparatus and then using these to display all the measurement data point-accurate, centred, overlaid. For this, the application of marks to the eye can be envisaged, for example colour dots to which each measuring apparatus or each measurement with the individual integrated measuring apparatus can orientate itself and refer. It is also possible to use the texture of the iris, in particular the unchangeable areas of the iris, or the texture of the veins in the sclera, as fixed parameters during the measurement. The treatment model is realized as a software module. By treatment model is meant that the software can calculate, on the basis of the measured or manually entered parameters, the ablation for each individual point of the cornea surface. A weighting of all the measurement values or parameters is carried out by the software. The software thus represents a central recording and evaluation tool. The ablation for each point of the cornea surface produces an ablation map, i.e. a "chart" with which the surface can be displayed. The device is preferably capable of displaying the ablation for each point graphically summarized as an ablation map.

The measuring instruments can also be arranged at least partly separately, their measurement results having to be imported manually into the device, or connected to the device by means of a data bus such as e.g. a serial cable so that their data can be automatically imported.

BRIEF DESCRIPTION OF THE DRAWINGS

Advantageous designs of the invention are explained further in the drawings. There is shown in.

DETAILED DESCRIPTION

Figure 1:
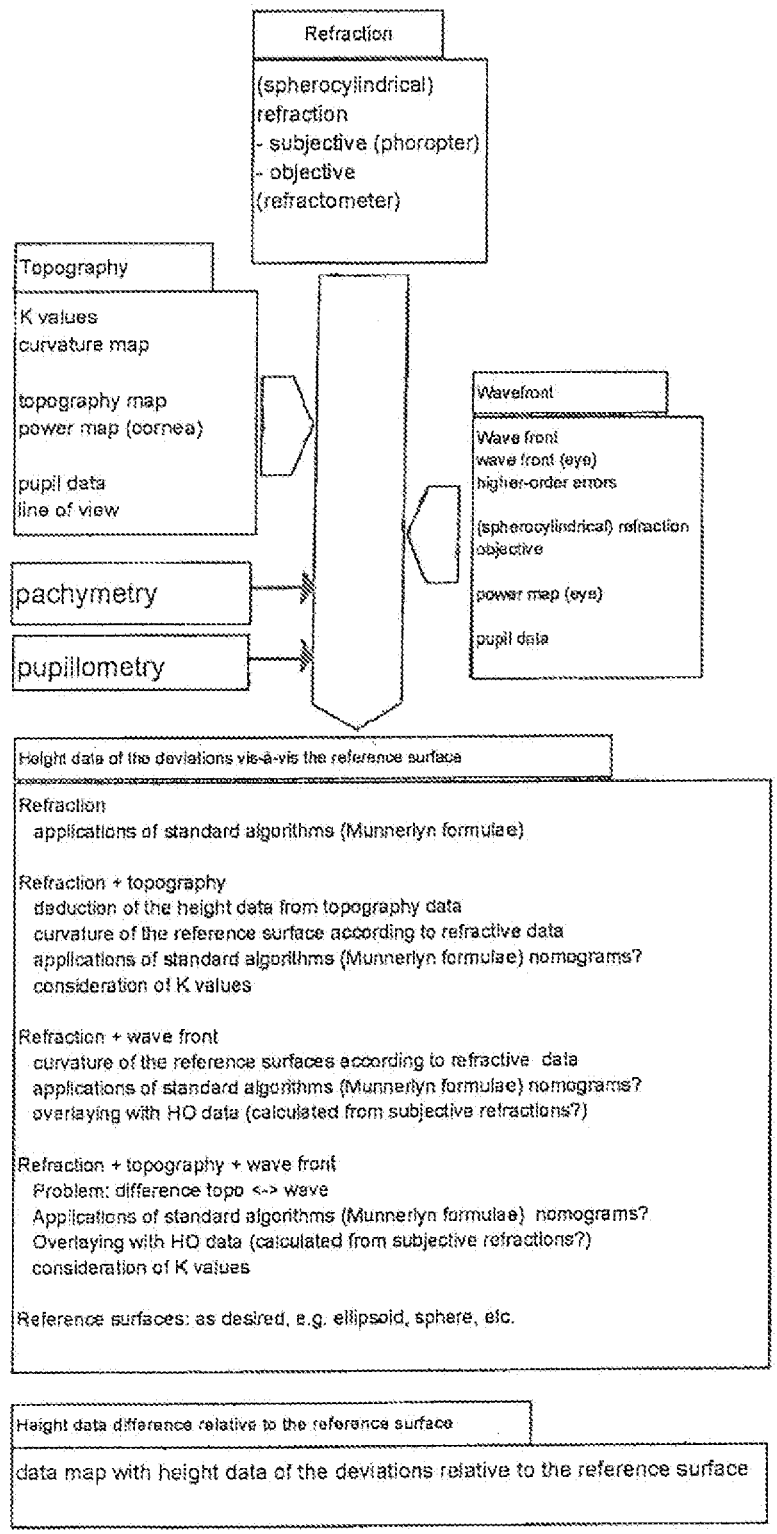
FIG. 1 a flowchart of the method.
Figure 1:
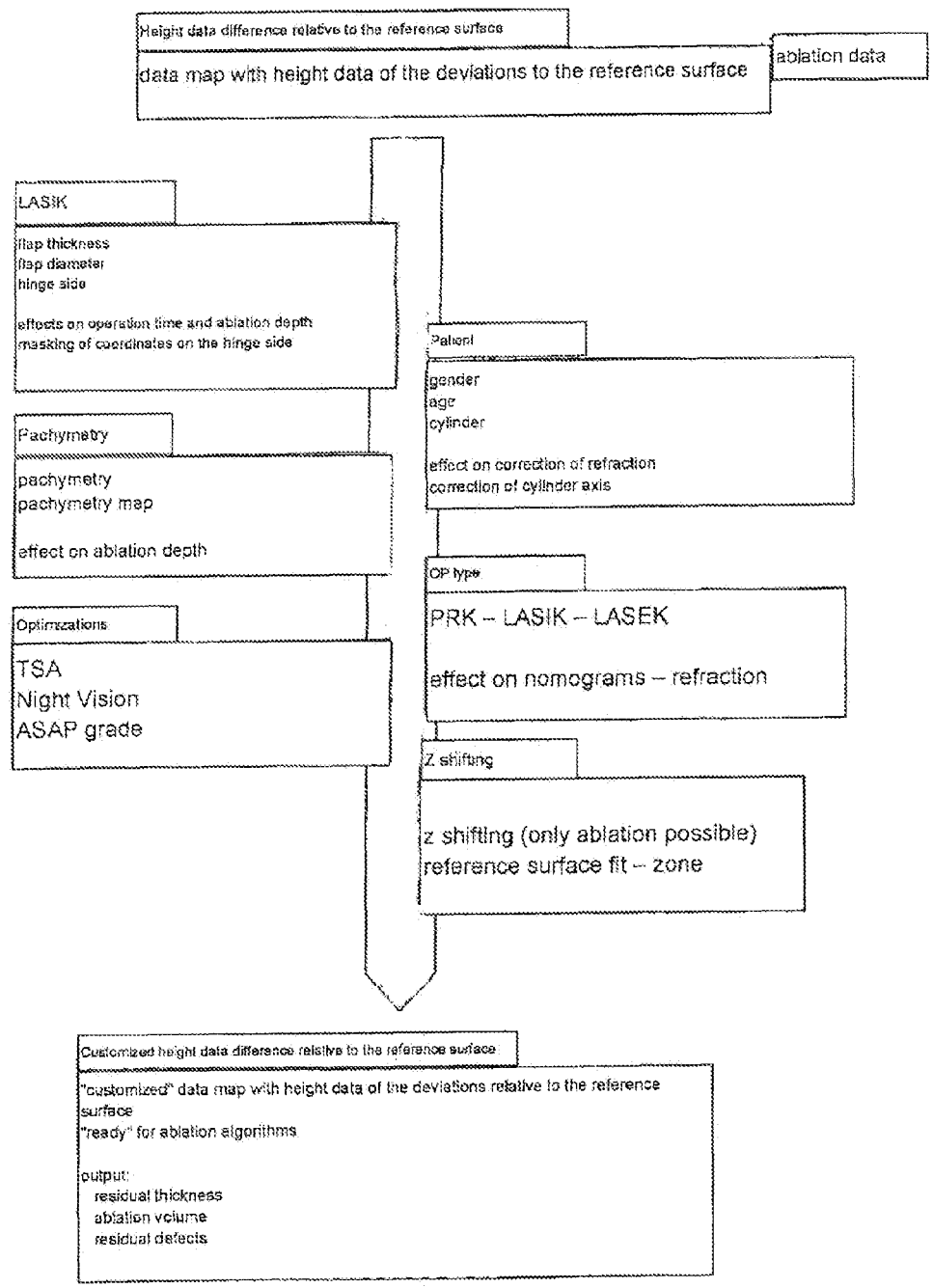
Figure 1:
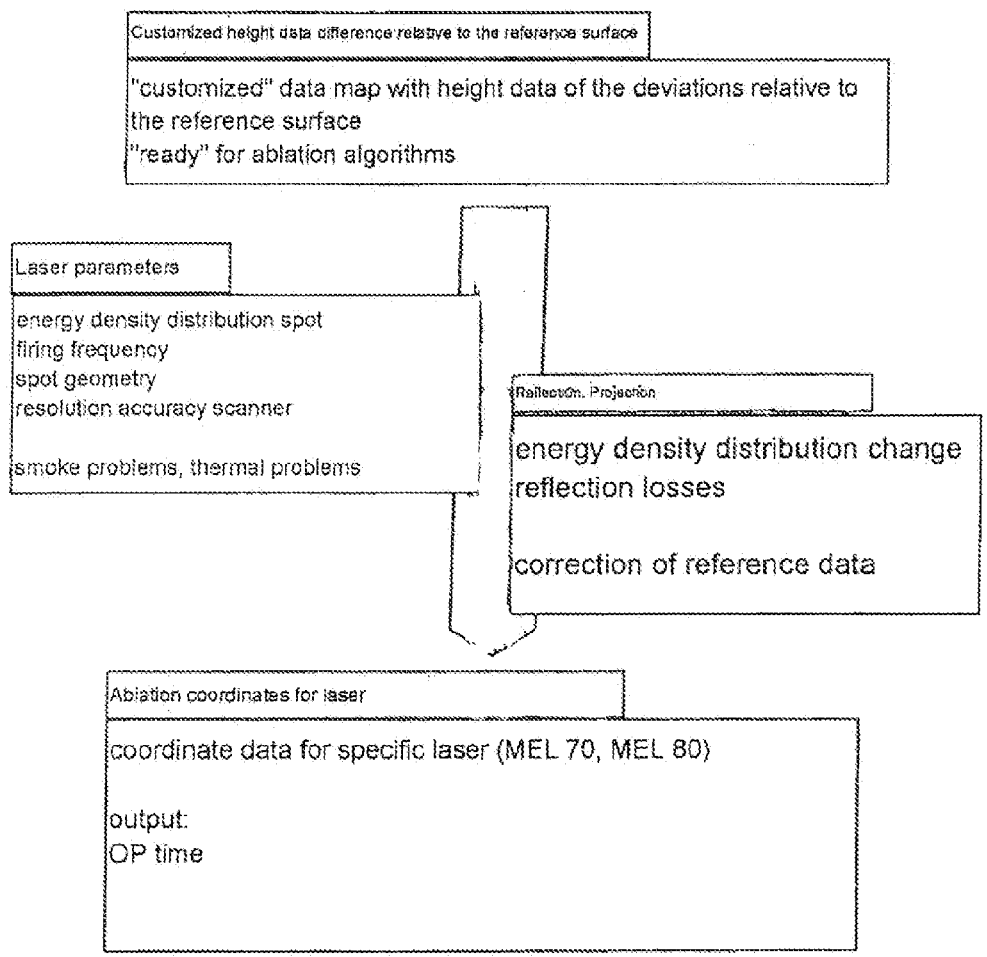

FIG. 1 shows a flowchart of the method according to the invention. Initially, the optical data of the eye are recorded in a first step. For this the topography is initially established in the form of K values, a curvature map, a topography map and a power map of the cornea. Pupil data and centring data such as the line of view (visual axis of the eye) are also included.

In a next step, objective and subjective refraction data, namely the spherical and cylindrical refraction of the patient, are established. Objective refraction data are data which are established exclusively by measuring with a measuring apparatus. This can be for example by means of a refractometer or aberrometer. Subjective refraction data are data which are based on the feedback from the patient, who reports whether a potential correction is found to be "better" or worse. This is achieved for example by using a phoropter which displays potential correction scenarios on which the patient comments.

With refractive correction of the cornea based on aberrometric wave-front data it must be taken into account that an aberrometer measurement is an objective measuring process. However, due to the physiological process of vision, the quality of the individual sight is ultimately fixed, not only by the objective optical quality of the optical system, the eye, but additionally by the subjectively evaluated visual faculty.

With the device according to the invention and the method according to the invention, it is provided to also allow, in addition to aberrometry, topography, pachymetry, pupillometry, fixing/centring, registration (this is a point-accurate allocation of the measurement data of the eye to position the therapeutic correction, e.g. via local marks on the cornea or significant structures of the eye such as veins or iris structures) and phoropter, a subjective evaluation of the refraction with the help of a phase-plate or adaptive phoropter and an acuity projector to play a part.

In a simplified method the subjective evaluation of the higher-order aberrations can be excluded, e.g. by means of Zernike polynomials, using the sphere and cylinder values determined with a refractometer and/or subjectively evaluated with a phoropter as a base data set for the refractive correction. In addition this base data set is supplemented by the objectively measured data of higher-order Zernike polynomials which are corrected by the spherical equivalent portions from the wave-front data. The higher aberration orders have a particular role in the production of aspherical lens profiles or correction profiles. The simplified method represented above can also be carried out directly on the basis of height data instead of the wave-front/data calculation based on Zernike polynomials. These aberrometer-aided height data are customary in the measurement data output of topography equipment and are obtained in aberrometers with the help of "zonal reconstruction". Compared with data exchange on the basis of Zernike polynomials, they guarantee a higher spatial resolution of the wave front. Uncertainties with regard to the correct wave-front reconstruction in polynomial description can be largely avoided depending on the resolution of the zonal reconstruction. So-called "repair cases" can thus be realized based on a complete data set of the overall optical system. Also on the basis of these wave-front height data, it must be taken into account within the framework of the described simplified method that in addition to the base data set the wave-front data can also be supplemented as equivalent portions without the spherical and cylindrical base portions.

In individually optimized treatment based on the method according to the invention, a higher quality of the refractive correction of the cornea is achieved in particular by combining the produced measurement data of the whole wave front and the topography of the cornea based on a polynomial breakdown, e.g. according to Zernike or Taylor and/or the height data. In this way, the refractive correction can be designed in consideration of the special characteristics of the different optical part-systems of the eye. Particular consideration is given to the cornea which delivers the main refracting power of the eye at approx. 80% and simultaneously forms the ablation target for refractive laser surgery. Thus in a simplified model the projection effects of the ablative laser spot on the spherical surface of the cornea can be taken into account for a radius of approx. 7.8 mm over a keratometric radius measurement of the cornea. A still more precise control of the ablation in consideration of the projective fluence variations of the laser spot on the cornea is obtained when the topography is taken into account. Thus not only can the ablation be controlled by the method according to the invention, in consideration of a keratometrically established radius of the cornea in order to balance out the projective fluence variations of the laser spot in particular at the margins of the ablation, but the topography data which describe the surface more accurately can also be used for this.

The higher-order aberrations are objectively established by means of a wave-front measurement. Known devices and methods for wave-front measurement can be used for this.

In a further step, height data of the deviations of the cornea surface relative to a reference surface are calculated from the thus-established refraction or topography data. They are established from refraction data, applying the standard algorithms, for example the Munnerlyn formulae. A sphere is used as assumed reference surface.

In a further step the height data are derived from the topography data. The curvature of the reference surface is established using the refraction data. Here too the data are calculated using standard algorithms such as Munnerlyn formulae. The K values are also taken into account here. An ellipsoid is used as assumed reference surface.

In a further step, the refraction data are linked to the data of the wave-front measurement. The curvature of the reference surfaces is established using the refractive data. The subjective refractions are calculated applying standard algorithms such as the Munnerlyn formulae and overlaying the thus-established data with high-order (HO) data. A sphere is used as assumed reference surface.

In a third step the refraction data are linked to the topography data and the data of the wave-front measurement. Here too these values are overlaid with high order data in consideration of the K values applying standard algorithms such as the Munnerlyn formulae. An ellipsoid is used here as assumed reference surface. The difference in the topography data vis-à-vis the data established with the wave front measurement is problematic.

In a further step the height data difference relative to the reference surface is now calculated. A chart (data map) is calculated with height data relative to the deviations to the reference surface. The height difference relative to the reference surface, and thus the tissue to be abraded is given for each point of the cornea surface.

When applying the LASIK procedure, the flap thickness, the flap diameter and the direction of the fold (hinge side) of the flap are determined. Furthermore, data relating to pachymetry, the thickness of the cornea, are included in the form of a pachymetry map. The effects of pachymetry on the ablation depth are determined. In addition, further patient data such as the age and the cylinder data of the patient are included. Effects on the correction of the refraction and correction of the cylinder axis are also calculated from these.

Depending on the method to be carried out, for example PRK or LASIK, process-typical effects on the nomograms and the refraction are established.

In addition certain optimizations are taken into account, e.g. TSA, Night Vision, ASAP grade. A reference surfaces fit is brought about in each zone with a Z shifting.

With the parameters shown above, patient-adapted (customized) height data differences relative to the reference surface are established from the height data difference relative to the reference surface. This results in an adapted data map with height data of the deviation relative to the reference surface. The ablation algorithms are realized with these data. This produces as a result the output of the residual thickness, the ablation volume and the residual defect.

In addition to the previously established data the influences of the laser parameters, in particular the energy density distribution, the firing frequency, the spot geometry and also the resolution accuracy of the scanner are taken into account. In addition the data with regard to smoke and thermal problems are incorporated.

In addition, reflection and projection data are established, in particular the change in energy density distribution and reflection losses. This yields correction data for the ablation target data.

Finally, ablation coordinates for the laser are issued, in this case coordination data for specific lasers (for example MEL 70).

The established and calculated data can be issued on a computer screen in the form of a graphic simulation. The simulation displays the cornea to be treated for example in different colours or similar in top view or in section so that the doctor in attendance can assess the whole procedure in advance.

Thus it is possible with this device or the electronic data-processing system which consists either of a networked or compact integrated measuring equipment system to record all the objective and subjective data of the optical refraction and geometry of the eye is such a way that they are stored or displayed overlaid centred and point-accurate in a fixed coordinates system of the eye.

What is claimed is:

1. A method for controlling a device for an ablation of a part of a human eye using laser irradiation, the control being exercised using an electronic data processing system, the method comprising:
    providing an ablation device;
    determining optic and geometrical data of the eye, wherein the determining includes establishing a pachymetry data of the eye;
    performing a graphic simulation of the ablation in the form of a graphic visualization; and
    controlling the device for the ablation according to the graphic visualization using the optic and geometrical data of the eye.

2. The method as recited in claim 1, further comprising inputting a plurality of treatment parameters manually using a central input/output device.

3. The method as recited in claim 2, further comprising determining a plurality of operating parameters, wherein the determining includes at least one of:
    a) establishing a topography data of the eye;
    b) establishing a refraction data of the eye;
    c) establishing a higher-order aberration data of the eye using wave-front measurement;
    d) establishing a pupillometry data;
    e) point-accurate overlaying of all the measurement data from a) through d) in a fixed coordinates system of the eye;
    f) calculating a height data of deviations relative to a reference surface;
    g) calculating a height data difference relative to the reference surface;
    h) calculating an adapted height data difference relative to the reference surface; and
    i) calculating ablation coordinates for the device, wherein the device includes a laser.

4. The method as recited in claim 3, wherein the establishing of the refraction data includes establishing at least one of a subjective and an objective refraction data.

5. The method as recited in claim 3, further comprising calculating a height data of deviations of a cornea surface of the eye relative to a reference surface using at least one of the topography data and the refraction data.

6. The method as recited in claim 5, further comprising determining a tissue to be abraded from the cornea of the eye using the height data of the deviations of the cornea surface.

7. The method as recited in claim 3, further comprising determining a result using the topography data, the result including at least one of a K value, a curvature map, a topography map, and a power map, and wherein the controlling the device for the ablation is performed using the result.

8. The method as recited in claim 3, wherein the establishing of the refraction data of the eye includes establishing at least one of spherical refraction data and cylindrical refraction data.

9. The method as recited in claim 3, wherein the reference surface is an ellipsoid.

10. The method as recited in claim 3, wherein a refraction reference surface of the refraction data is a spheroid.

11. The method as recited in claim 1, wherein the device for ablation includes at least one of a laser and a wave-front measurement device.

* * * * *